(12) United States Patent
Nakao et al.

(10) Patent No.: US 6,302,871 B1
(45) Date of Patent: Oct. 16, 2001

(54) DISPOSABLE PULL-ON GARMENT HAVING IMPROVED DISPOSAL HANDLING AFTER SOIL

(75) Inventors: Chikayo Nakao, Kobe; Craig Andrew Hawkins, Ashiya, both of (JP)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 09/424,133

(22) PCT Filed: May 30, 1997

(86) PCT No.: PCT/US97/09262

§ 371 Date: Nov. 18, 1999

§ 102(e) Date: Nov. 18, 1999

(87) PCT Pub. No.: WO98/53780

PCT Pub. Date: Dec. 3, 1998

(51) Int. Cl.$^7$ .................................................. A61F 13/15
(52) U.S. Cl. ................ 604/385.13; 604/391; 604/389
(58) Field of Search ........................ 604/385.13, 389; 428/343

(56) References Cited

U.S. PATENT DOCUMENTS

| | | |
|---|---|---|
| 4,747,846 | 5/1988 | Boland et al. ............... 604/38 A |
| 5,246,433 * | 9/1993 | Hasse et al. ................ 604/396 |
| 5,531,732 * | 7/1996 | Wood ......................... 604/391 |
| 5,575,784 * | 11/1996 | Ames-Ooten et al. ........ 604/385.1 |

FOREIGN PATENT DOCUMENTS

| | | |
|---|---|---|
| 0 570 980 B | 11/1993 | (EP) . |
| 0 657 153 B | 6/1995 | (EP) . |
| 0 768 074 A | 4/1997 | (EP) . |
| 2 244 422 A | 12/1991 | (GB) . |

* cited by examiner

Primary Examiner—John G. Weiss
Assistant Examiner—Jacqueline F Stephens
(74) Attorney, Agent, or Firm—Michael S. Kolodesh; David M. Weirich; Ken K. Patel (57) ABSTRACT

The disposable pull-on garment of the present invention comprises a chassis having a front region, a back region and a crotch region between the front region and the back region. The chassis comprises a liquid pervious topsheet, a liquid impervious backsheet associated with the topsheet, and an absorbent core disposed between the topsheet and the backsheet. The disposable pull-on garment of the present invention further comprises front side panels extending laterally outwardly from each side of the chassis in the front region; back side panels extending laterally outwardly from each side of the chassis in the back region; seam panels (66) each extending laterally outwardly from each of the front and back side panels; seams each joining the corresponding seam panels in an overlap manner to make an overlapped seam structure (32), thereby forming two leg openings and a waist opening; and a disposable means (31) joined to the at least one of the front and back side panels for allowing the pull-on garment to be secured in a configuration that provides a convenient disposal.

10 Claims, 9 Drawing Sheets

DISPOSABLE PULL-ON GARMENT HAVING IMPROVED DISPOSAL HANDLING AFTER SOIL

FIELD

The present invention relates to disposable pull-on garments. Examples of such disposable pull-on garments include disposable underwear, pull-on diapers, training pants, and disposable panties for menstrual use. The present invention more particularly relates to unitary disposable absorbent pull-on garments such as pull-on diapers, training pants, incontinent pull-on briefs, and the like, which provide improved disposal handling after its soil.

BACKGROUND

Infants and other incontinent individuals wear disposable absorbent articles such as diapers to receive and contain urine and other body exudes. Absorbent garments having fixed sides (e.g., training pants or pull-on diapers) have become popular for use on children able to walk and often who are toilet training. These training pants have side panels which edges are seamed together to form two leg openings and a waist opening. These pants need to fit snugly about the waist and legs of the wearer without drooping, sagging or sliding down from its position on the torso to contain body exudes.

After a training pant or pull-on diaper is soiled by urine or body exudes, it is removed from the wearer's body by tearing open the seams of the side panels. The removed training pant or pull-on diaper then is folded so that the soiled portion is wrapped inside for disposal. To prevent the soiled training pant or pull-on diaper from being unfolded and/or to keep the soiled portion inside, it is desired that such training pant or pull-on diaper has a disposal means which secures or keeps the folded diaper in the folded state. Examples of such training pants are disclosed in U.S. Pat. No. 5,575,784 to Ames-Ooten et al. on Nov. 19, 1996, and European Patent Publication Nos. EP623330 and EP0732094.

However, the existence of such disposal means sometimes tends to cause a leakage of contained urine or body exudes from the sides of the folded diaper especially when the side edges of the diaper are not appropriately folded inwardly. Further, such disposal means also tends to be an obstacle to the wearer's movement and/or decrease the diaper's good appearance.

SUMMARY

The present invention is directed to a disposable pull-on garment. The disposable pull-on garment of the present invention comprises a chassis having a front region, a back region and a crotch region between the front region and the back region. The chassis comprises a liquid pervious topsheet, a liquid impervious backsheet associated with the topsheet, and an absorbent core disposed between the topsheet and the backsheet. The disposable pull-on garment of the present invention further comprises front side panels extending laterally outwardly from each side of the chassis in the front region; back side panels extending laterally outwardly from each side of the chassis in the back region; seam panels each extending laterally outwardly from each of the front and back side panels; seams each joining the corresponding seam panels in an overlap manner to make an overlapped seam structure, thereby forming two leg openings and a waist opening; and a disposal means joined to the at least one of the front and back side panels for allowing the pull-on garment to be secured in a configuration that provides a convenient disposal.

These and other features, aspects, and advantages of the present invention will become evident to those skilled in the art from a reading of the present disclosure.

BRIEF DESCRIPTION OF THE DRAWINGS

While the specification concludes with claims particularly pointing out and distinctly claiming the invention, it is believed that the invention will be better understood from the following description of preferred embodiments which is taken in conjunction with the accompanying drawings and which like designations are used to designate substantially identical elements, and in which:

DETAILED DESCRIPTION

All cited references are incorporated herein by reference in their entireties. Citation of any reference is not an admission regarding any determination as to its availability as prior art to the claimed invention.

As used herein, the term "pull-on garment" refers to articles of wear which have a defined waist opening and a pair of leg openings and which are pulled onto the body of the wearer by inserting the legs into the leg openings and pulling the article up over the waist. The term "disposable" is used herein to describe garments which are not intended to be laundered or otherwise restored or reused as a garment (i.e., they are intended to be discarded after a single use and, preferably, to be recycled, composted or otherwise disposed of in an environmentally compatible manner). A "unitary" pull-on garment refers to pull-on garments which are formed of separate parts united together to form a coordinated entity, but the side panels are not separate elements joined to a separate chassis in that the side panels are formed by at least one layer which also forms the central panel or chassis of the garment (i.e., the garment does not require separately manipulative panels such as a separate chassis and separate side panels). The pull-on garment is also preferably "absorbent" to absorb and contain the various exudates discharged from the body. A preferred embodiment of the pull-on garment of the present invention is the unitary disposable absorbent pull-on garment, pull-on diaper 20, shown in FIG. 1. As used herein, the term "pull-on diaper" refers to pull-on garments generally worn by infants and other incontinent individuals to absorb and contain urine and feces. It should be understood, however, that the present invention is also applicable to other pull-on garments such as training pants, incontinent briefs, feminine hygiene garments or panties, and the like. As used herein, the term "panel" is used herein to denote an area or element of the pull-on garment. (While a panel is typically a distinct area or element, a panel may coincide (functionally correspond) somewhat with an adjacent panel.) As used herein, the term "joined" or "joining" encompasses configurations whereby an element is directly secured to the other element by affixing the element directly to the other element, and configurations whereby the element is indirectly secured to the other element by affixing the element to intermediate member(s) which in turn are affixed to the other element.

Figure 1:
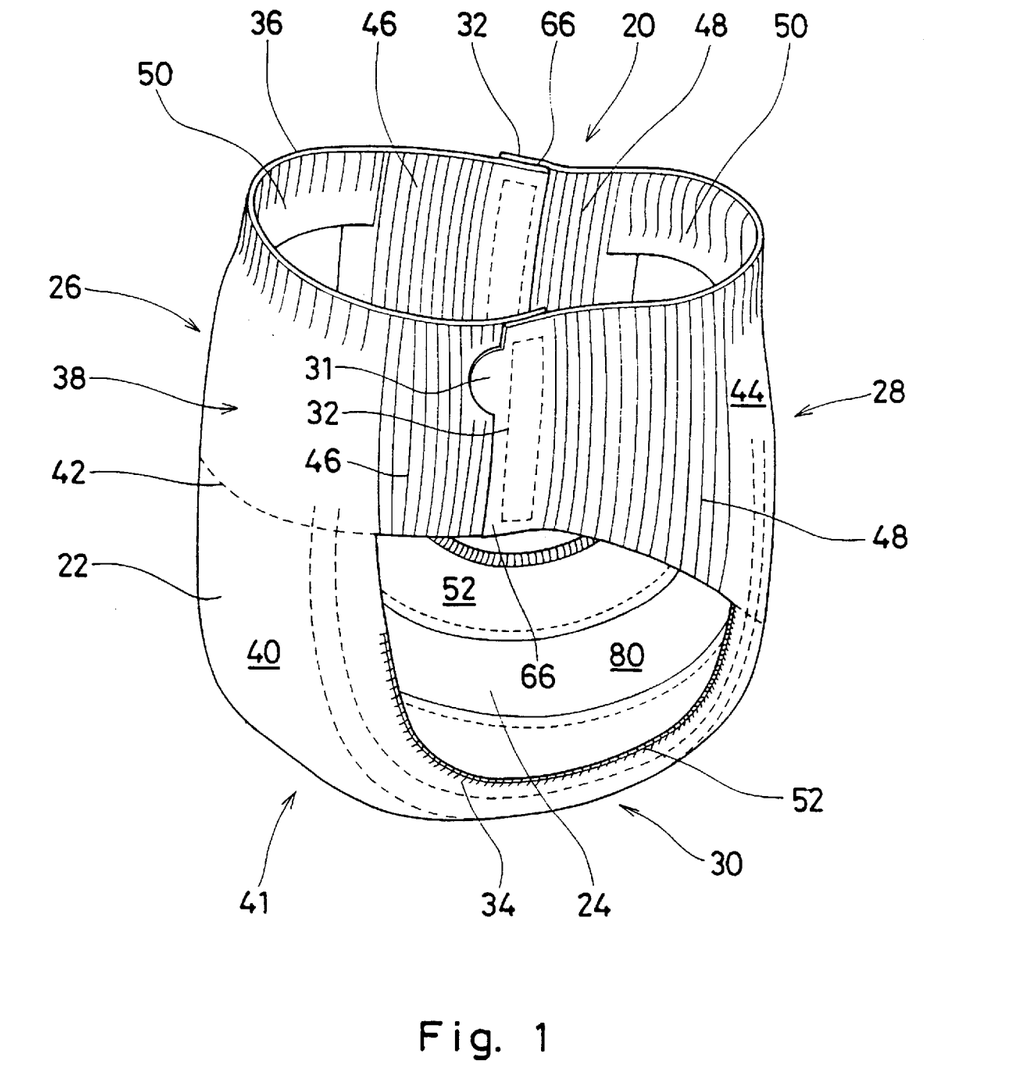
FIG. 1 is a perspective view of a preferred embodiment of the disposable pull-on garment of the present invention in a typical in use configuration.

Referring to FIG. 1, the pull-on diaper 20 comprises a chassis 41 having a front region 26, a back region 28 and a crotch region 30 between the front region 26 and the back region 28. The chassis 41 comprises a liquid pervious topsheet 80, a liquid impervious backsheet 22 associated with the topsheet 80, and an absorbent core 84 (not shown in FIG. 1) disposed between the topsheet 80 and the backsheet 22. The pull-on diaper 20 further comprises front side panels 46 each extending laterally outwardly from the corresponding side of the chassis 41 in the front region 26, and back side panels 48 each extending laterally outwardly from the corresponding side of the chassis 41 in the back region 28. The pull-on diaper 20 further comprises seam panels 66 each extending laterally outwardly from each of the front and back side panels 46 and 48; and tear open tabs 31 each extending laterally outwardly from the seam panels 66. Preferred examples of the pull-on diaper 20 are disclosed in U.S. Pat. No. 5,569,234 to Buell et al. on Oct. 29, 1996.

The front and back side panels 46 and 48 of the present invention can be any members which extend laterally outwardly from the corresponding side edges of the chassis 41. In preferred embodiments, each of the front and back side panels 46 and 48 is a projected member which projects laterally outwardly from the chassis 41 (more clearly shown in FIGS. 2 and 3). Preferably, the front side panels 46 and back side panels 48 are unitary elements of the pull-on diaper (i.e., they are not separately manipulative elements secured to the pull-on diaper, but rather are formed from and are extensions of one or more of the various layers of the pull-on diaper.) More preferably, each of the seam panels 66 is an extension of the corresponding front and back side panels 46 and 48, or at least one of the component elements used therein, or any other combination of the elements. Preferably, each of the tear open tabs 31 is an extension of the corresponding seam panels 66 or at least one of their component elements used therein, or any other combination of the elements. In preferred embodiments, the front and side panels 46 and 48 are continuous members which continuously extend from the chassis 41. More preferably, at least one, preferably both of the front and back side panels 46 and 48, comprises a continuous sheet or film material 42 which is a part of the chassis 41 and continuously extends from the chassis 41. In alternative embodiments, the front and side panels 46 and 48 are discrete members (not shown in the figures) which are attached to the side edges of the chassis 41.

In a preferred embodiment, the front and back side panels 46 and 48 are elastically extensible in at least the lateral direction. As used herein, the term "elastically extensible" means a segment or portion that will elongate in at least one direction (preferably the lateral direction for the side panel) when tensional forces (typically lateral tensional forces for the side panel) are applied, and will return to about its previous size and configuration when the tensional forces are removed. More preferably, the front and back side panels 46 and 48 are elastically extensible both in the lateral and longitudinal directions.

The pull-on diaper 20 further comprises seams 32 each joining the corresponding seam panels 66 in an overlap manner to make an overlapped seam structure, thereby forming two leg openings 34 and a waist opening 36. The bonding of the seams 32 of the present invention can be performed by any suitable means known in the art appropriate for the specific materials employed in the seam panels. Thus, sonic sealing, heat sealing, pressure bonding, adhesive or cohesive bonding, sewing, autogeneous bonding, and the like may be appropriate techniques. Preferably, the seam panels 66 are joined by a pattern of heat/pressure or ultrasonic welds.

A continuous belt 38 is formed about the waist opening 36. The continuous belt 38 acts to dynamically create fitment forces and to distribute the forces dynamically generated during wear. The pull-on diaper 20 thus preferably comprises a chassis layer 40; a first belt layer 42; and a second belt layer 44. Preferably, an elastic waist feature 50 is provided in both the front region 26 and the back region 28. The pull-on diaper 20 additionally comprises elastic leg features 52. More preferably, apertures or vents (not shown) are provided in at least the side panels 46 and 48 of the pull-on diaper 20 to provide breathability and ventilation. Because the first belt layer 42 and the second belt layer 44 are preferably nonwoven webs having the appearance of cloth and the chassis layer 40 is preferably a plastic film, the pull-on diaper 20 has a unique aesthetic feature in that it is perceived by caregivers and wearers to have a garment-like comfort and feel in the waist regions while having a perceived containment benefit in the crotch region.

The continuous belt 38 is elastically extensible in the side panels 46 and 48 to provide a more comfortable and contouring fit by initially conformably fitting the pull-on diaper 20 to the wearer and sustaining this fit throughout the time of wear well past when it has been loaded with exudates by distributing forces along both the waist and legs since the sides of the pull-on diaper can expand and contract. The continuous belt 38 may be formed from a number of different materials and layers as defined below.

Figure 2:
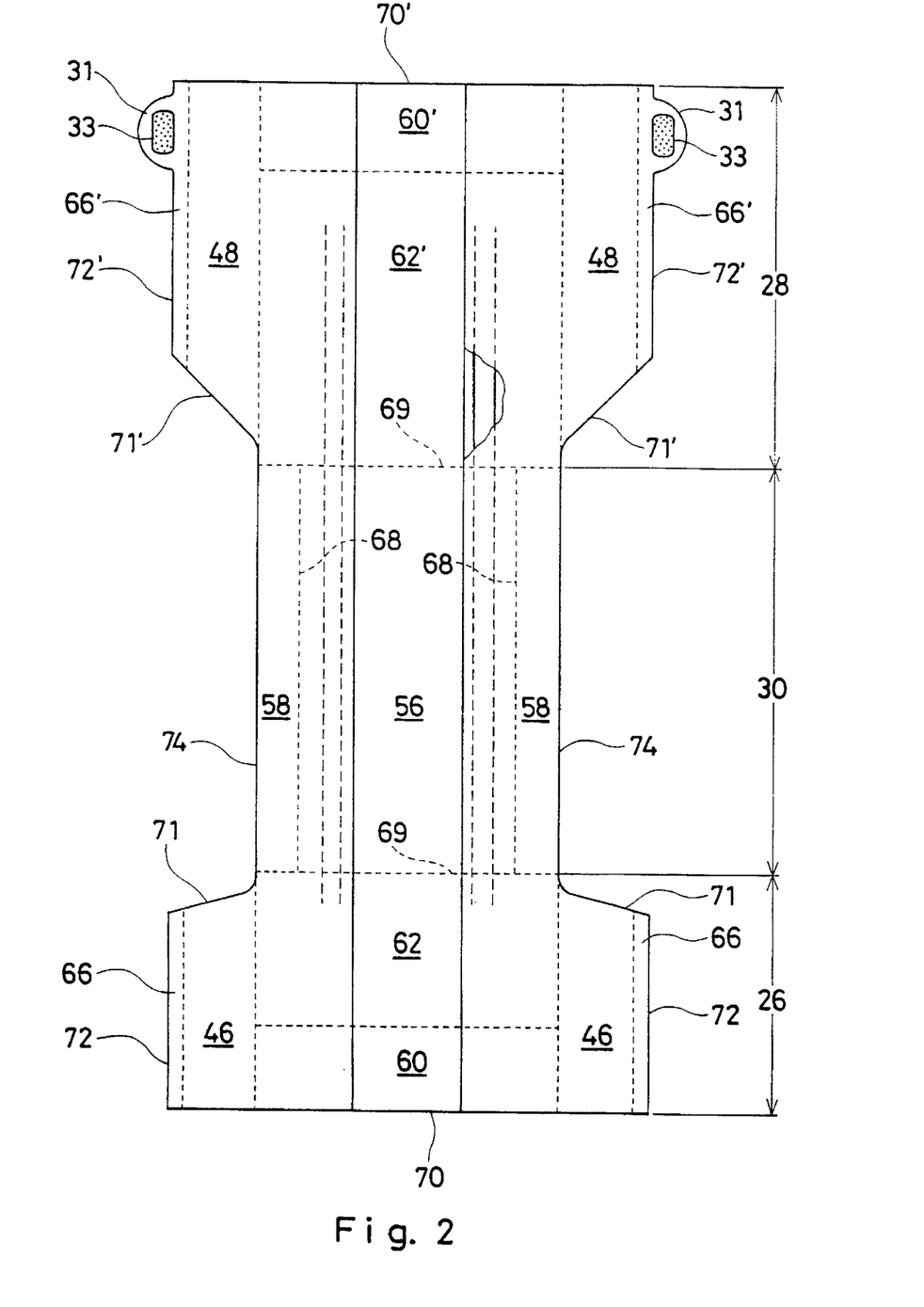
FIG. 2 is a simplified plan view of the embodiment shown in FIG. 1 in its flat uncontracted condition showing the various panels or zones of the garment.

FIG. 2 shows a simplified plan view of the pull-on diaper 20 of FIG. 1 in its flat-out, uncontracted state depicting the various panels and their positioning with respect to each other. The pull-on diaper 20 has the crotch region 30 comprising a main panel 56 and a pair of leg flap panels 58; the front region 26 comprising a central panel comprising a waistband panel 60 and a medial panel 62, the front side panels 46, and the seam panels 66; and the back region 28 comprising a central panel comprising a waistband panel 60' and a medial panel 62', the back side panels 48. the seam panels 66', and the tear open tabs 31. The absorbent core 84 (not shown in FIG. 2) is generally positioned within the main panel 56, since exudates are typically discharged in this region, although the absorbent core 84 will typically extend into the medial panels 62 and 62' of the belt.

In the embodiment shown in FIG. 2, a leg flap panel 58 extends generally laterally outwardly from and along each side edge 68 of the main panel 56. Each leg flap panel 58 generally forms at least a portion of the elastic leg feature 52 (shown in FIG. 3). The continuous belt 38 (the front region 26 and the back region 28) extends generally longitudinally outwardly from and along each lateral edge 69 of the crotch region 30 (the main panel 56 and the leg flap panel 58). In the front region 26, the medial panel 62 extends generally longitudinally outwardly from and along the lateral edge 69 of the crotch region 30. The waistband panel 60 extends generally longitudinally outwardly from and along the medial panel 62. The side panels 46 each extend generally laterally outwardly from and along the central panel (the panels 60 and 62). The seam panels 66 each extend generally laterally outwardly from and along the respective side panel 46. In the back region 28, the medial panel 62' extends generally longitudinally outwardly from and along the other lateral edge 69 of the crotch region 30. The waistband panel 60' extends generally longitudinally outwardly from and along the medial panel 62'. The side panels 48 each extend generally laterally outwardly from and along the central panel (the panels 60' and 62'). The seam panels 66' each extend generally laterally outwardly from and along the respective side panel 48. The tear open tabs 31 each extend generally laterally outwardly from and along the respective seam panels 66'. Disposal means 33 are provided on the respective tear open tabs 31. The front region 26, in addition to its panels, also has an end edge 70, leg edges 71, and side edges 72. The back region 28, in addition to its panels, also has an end edge 70', leg edges 71', and side edges 72'. The crotch region 30 has leg edges 74.

The waistband panel 60 is preferably elastically extensible, more preferably elastically contractible or gathered, to better fit the pull-on diaper 20 in the central part of the waist opening 36. The medial panel 62 is not gathered in order to maintain the integrity of the absorbent core 84 during use. Although the medial panels 62 and 62' may be elastically extensible (but not gathered), they are preferably not extensible.

Figure 3:
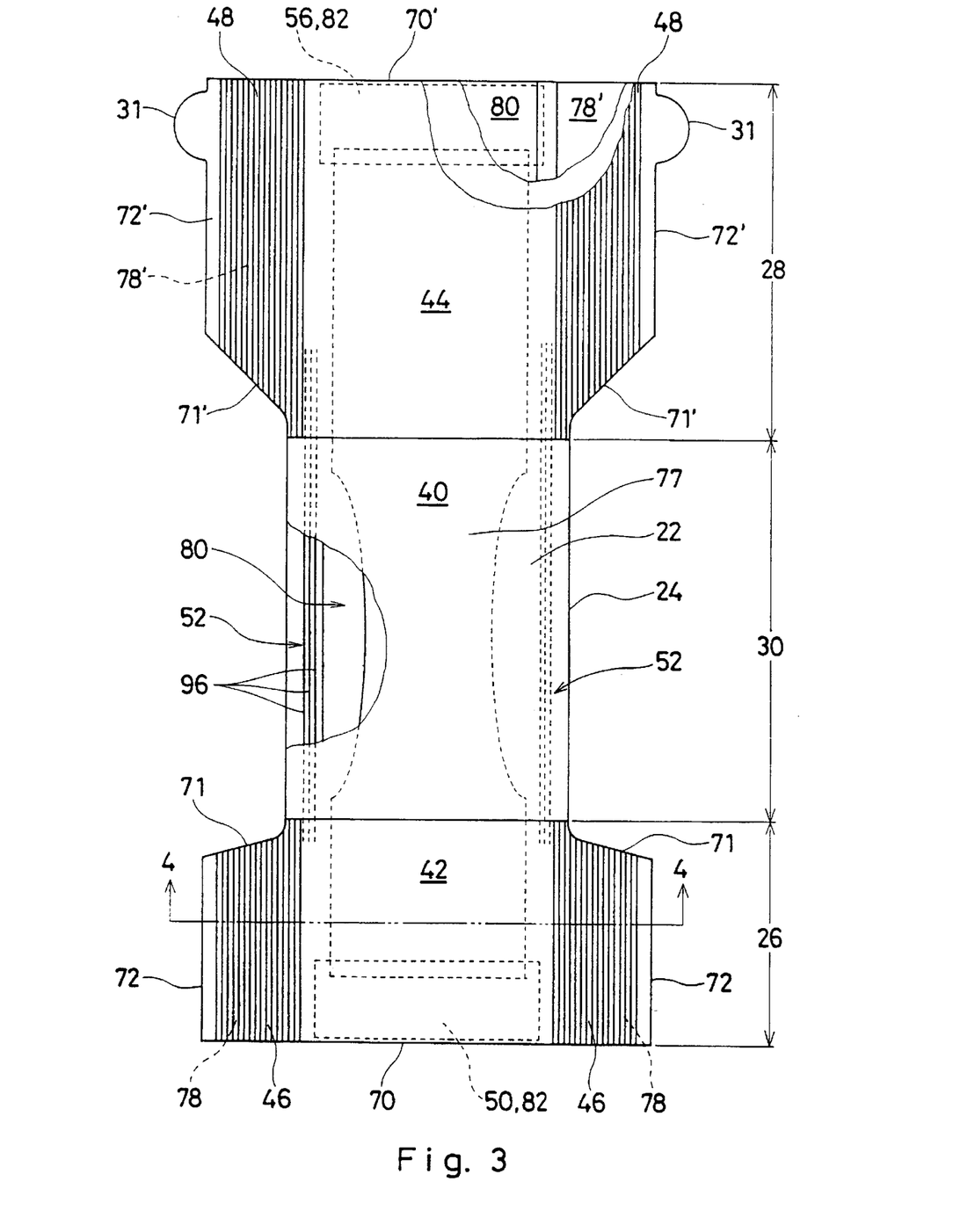
FIG. 3 is a plan view of the embodiment shown in FIG. 1 in its flat uncontracted condition showing the outer surface and having portions cut away to reveal underlying structure.

FIG. 3 is a partially cut-away plan view of the pull-on diaper 20 of FIG. 1 in its flat-out, uncontracted state (i.e., with elastic induced contraction pulled out except in the side panels 46 and 48 are left in their relaxed condition) with the backsheet 22 facing the viewer, prior to the front region 26 and the back region 28 being joined together by the seams 32. The backsheet 22 of the pull-on diaper 20 comprises that portion which is positioned away from the wearer's body during use. In the embodiment shown, the backsheet 22 of the pull-on diaper 20 comprises the first belt layer 42 in the front region 26, the second belt layer 44 in the back region 28, and the chassis layer 40 in the crotch region 30. (The inner surface 24 of the diaper is opposed to the backsheet 22 and comprises that portion of the diaper which is positioned adjacent to the wearer's body during use.)

In the embodiment shown in FIG. 3, the chassis layer 40 preferably comprises a continuous sheet or web which defines the front region 26, the back region 28, and the crotch region 30. Thus, the chassis layer 40 is the primary stratum or layer of the pull-on diaper. (As used herein, the term "layer" does not necessarily limit the element to a single strata of material in that a layer may actually comprise laminates or combinations of sheets or webs of the requisite type of materials.) The chassis layer 40 has an inner surface 76 (not shown in FIG. 3) and an outer surface 77. The inner surface 76 and outer surface 77 of the chassis layer 40 correspond in their orientation with the inner surface 24 and the backsheet 22 of the pull-on diaper 20. Since the chassis layer 40 preferably defines the front region 26, the back region 28, and the crotch region 30, the chassis layer 40 also has corresponding regions and panels as previously defined. (For simplicity, these regions and panels are denoted in the drawings by the same reference numerals as the corresponding pull-on diaper regions and panels as shown in FIG. 2.) The first belt layer 42 is positioned on the outer surface 77 of the chassis layer 40 in the front region 26 and extends continuously laterally across the front region 26 from one side edge 72 to the other side edge 72 and longitudinally from the end edge 70 to at least the leg edges 71. The first belt layer 42 is preferably joined to the chassis layer 40. The second belt layer 44 is positioned on the outer surface 77 of the chassis layer 40 in the back region 28 and extends continuously laterally across the back region 28 from one side edge 72' to the other side edge 72' and from the end edge 70' to at least the leg edges 71'. The second belt layer 44 is preferably joined to the chassis layer 40. Thus, each belt layer in combination with the chassis layer 40 forms a continuous belt 38 (as shown in FIG. 1) about the waist of the wearer. As will be detailed below, this belt has various elastic extension properties in various zones to enhance the fit and containment of the pull-on diaper 20.

Elastically extensible stretch laminates are formed in the respective side panels 46 and 48 of both the front region 26 and the back region 28. Each front side panel 46 at least comprises the portion of the first belt layer 42 in the side panel and an elastic panel member 78 joined thereto, and, in this particular embodiment, the portion of the chassis layer 40 forming the side panel. Preferably, the elastic panel member 78 is positioned between the chassis layer 40 and the first belt layer 42, and more preferably extends longitudinally from the end edge 70, most preferably to the leg edge 71. Each rear side panel 48 at least comprises the portion of the second belt layer 44 in each side panel and an elastic panel member 78' joined thereto, and, in this particular embodiment, the portion of the chassis layer 40 forming the side panel. Preferably, the elastic panel member 78' is positioned between the chassis layer 40 and the second belt layer 44, and more preferably extends longitudinally from the end edge 70', most preferably to the leg edge 71'. In the pull-on diaper embodiment shown in FIG. 3, each side panel preferably further comprises a portion of the topsheet 80 (the barrier layer) in the side panel. Each side panel is mechanically stretched or drawn (designated by the strain lines) to allow the side panel to be elastically extensible in at least the lateral direction. (The lateral direction (x direction or width) is defined as the direction parallel to the lateral centerline of the pull-on diaper; the longitudinal direction (y direction or length) is defined as the direction parallel to the longitudinal centerline; and the axial direction (z direction or thickness) is defined as the direction extending through the thickness of the pull-on diaper.)

An elastic waist feature 50 is provided in the waistband panel 60 of the front region 26 or the waistband panel 60' of the back region 28, or preferably both the front region 26 and the back region 28. The elastic waist feature 50 provides an elastically extensible member, preferably a gathered elastically contractible member, to dynamically fit and conform to the waist of the wearer in the central panels. In the embodiment shown, the elastic waist feature 50 preferably comprises a unitary waistcap/waistband 82 operatively joined in the waistband panel in an elastically contractible condition, preferably to the primary layer of the topsheet 80. The unitary waistcap/waistband 82 acts as a barrier to the leakage of exudates out of the waist opening of the pull-on diaper 20 as well as a contractible waistband to provide fit of the pull-on diaper 20 about the waist of the wearer. In the most preferred embodiments, the unitary waistcap/waistband is also breathable to allow venting of water vapor out of the pull-on diaper adjacent the waist opening.

In the embodiment shown in FIG. 3, the pull-on diaper 20 is also provided with elastic leg features 52 to improve fit at the legs in the crotch region 30. The pull-on diaper 20 additionally comprises a topsheet 80 and an absorbent core 84 (not shown) positioned between the topsheet 80 and the chassis layer 40 to provide an absorbent assembly that cooperates with the continuous belt to contain discharged exudates.

Figure 4:
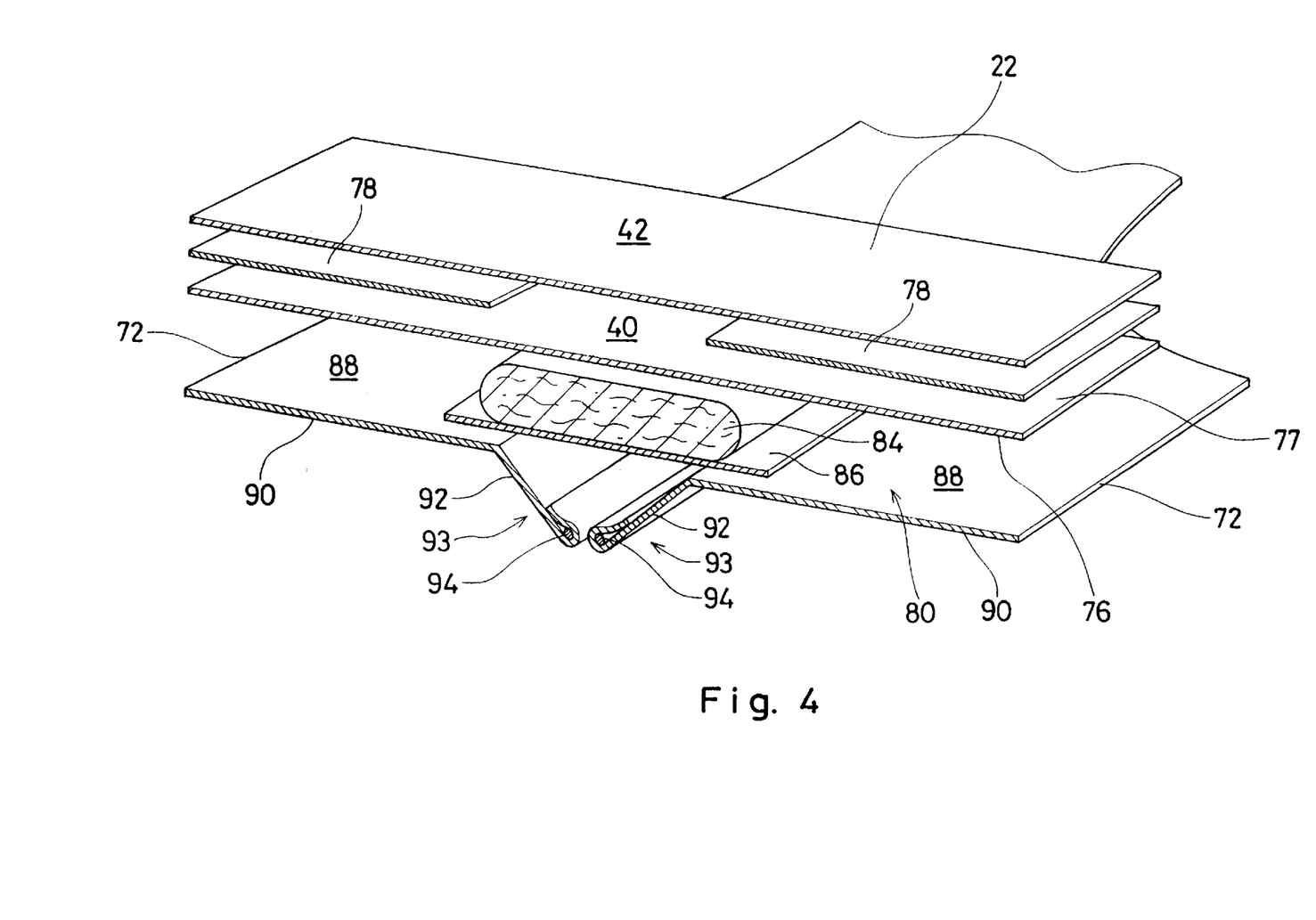
FIG. 4 is a fragmentary view of the pull-on garment shown in FIG. 3 taken along section line 4—4 of FIG. 3.

FIG. 4 is a cross-sectional perspective view of the pull-on diaper 20 taken along the line 4—4 of FIG. 3 in the front region 26. The chassis layer 40 is shown to form the primary strata or layer of the pull-on diaper 20 and has an inner surface 76 and an outer surface 77. The first belt layer 42 is positioned on the outer surface 77 of the chassis layer 40 to form the backsheet 22 of the pull-on diaper 20 in the front region 26. The elastic panel members 78 are preferably positioned between the first belt layer 42 and the chassis layer 40. The topsheet 80 is positioned on and joined to the inner surface 76 of the chassis layer 40. The topsheet 80 preferably comprises a liquid pervious primary layer 86 and two barrier layers 88. The barrier layers 88 extend laterally outwardly from the primary layer 86 to the side edges 72. Each barrier layer 88 comprises a flap portion 90 and a stand-up portion 92. The stand-up portion 92 is not attached to the primary layer 86 to allow the gathering forces of the elastic spacing member(s) 94 to cause the stand-up portion 92 to stand up away from the surface of the primary layer 86 to form a barrier cuff 93 which is a barrier or wall in use. The flap portion 90 extends laterally outwardly from the stand-up portion 92 (the proximal edge) to the side edge 72. The absorbent core 84 is preferably positioned between the primary layer 86 and the chassis layer 40. The construction of the back region 28 is preferably identical to the construction of the front region 26.

Figure 5:
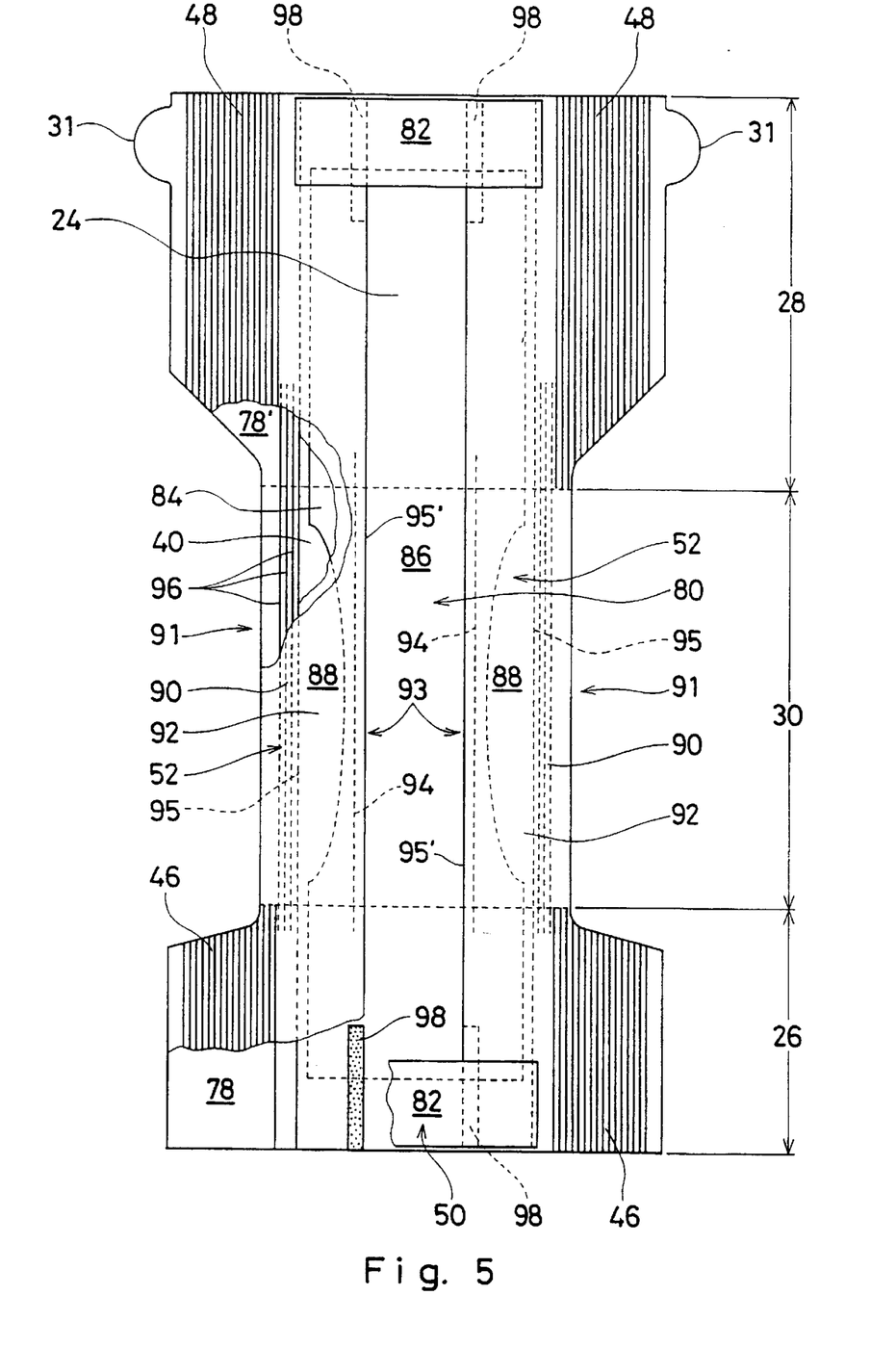
FIG. 5 is a plan view of the pull-on garment shown in FIG. 1 in its flat uncontracted condition showing the inner surface and having portions cut away to reveal underlying structure.

FIG. 5 is a partially cut-away plan view of the pull-on diaper 20 shown in FIG. 1 in its flat-out, uncontracted state (i.e., with elastic induced contraction pulled out except in the side panels wherein the side panels are left in their relaxed condition) with the inner surface 24 of the pull-on diaper 20 facing the viewer, prior to the front region 26 and the back region 28 being joined together by the searns. In order to provide the necessary absorbency to contain body exudates, the pull-on diaper 20 comprises a liquid pervious topsheet 80 and an absorbent core 84 positioned between the topsheet 80 and the chassis layer 40. In the embodiment shown in FIG. 5, the topsheet 80 preferably comprises three distinct layers joined together. A liquid pervious primary layer 86 is positioned over the absorbent core 84 to rapidly absorb liquids into the product. Barrier layers 88 are joined to the primary layer 86 and are preferably drawable, more preferably hydrophobic, to allow the side panels to be mechanically stretched without ripping or tearing while providing barrier cuffs 93 along the sides of the pull-on diaper 20. The barrier layers 88 have a flap portion 90 and a channel or stand-up portion 92 to provide the various components of the elastic leg features 52. The elastic leg features 52 preferably comprise a gasketing cuff 91 and a barrier cuff 93. The gasketing cuff 91 is preferably formed by one or more elastic leg members 96 operatively joined to the chassis layer 40, the barrier layer 88, or both, preferably between the chassis layer 40 and the flap portion 90 of the barrier layer 88 in the leg flap panel of the crotch region 30. The barrier cuff 93 is preferably formed by a flap (the stand-up portion 92 of the barrier layer 88), closing means 98 for securing the longitudinal ends of the stand-up portion 92 to the primary layer 86, and an elastic spacing member 94 operatively joined to the stand-up portion 92.

The elastic extensibility in the side panels 46 and 48 may be provided by a number of different materials and configurations. Various components of the belt (e.g., the belt layers or the chassis layer) may comprise conventional elastic materials or the side panels of the belt may be constructed from a number of different elastic laminate structures. For example, the side panels of the belt can comprise an elastic material operatively joined to one or more inelastic components (belt layer or chassis layer or both) in an elastically contractible condition such as is described in U.S. Pat. No. 3,860,003 entitled "Contractable Side Portions For A Disposable Diaper" issued to Buell on Jan. 14, 1975. Alternatively, the side panels can comprise a structural elastic-like film (SELF) web such as described in WO 95/03765, "Web Materials Exhibiting Elastic-like Behavior", The Procter & Gamble Company, published Feb. 9, 1995. While the side panels of the belt may be constructed from a number of different extensible or elastic materials as are known in the art, one or more, and preferably each, of the side panels of the belt are constructed of a stretch laminate.

In a preferred embodiment of the present invention, an elastic panel member 78 is operatively joined in the side panels 46 and 48, preferably between the chassis layer 40 and the belt layers 42 and 44, to allow the side panels 46 and 48 to be elastically extensible in at least the lateral direction. Elastomeric materials which have been found to be especially suitable for use as the elastic panel members (especially for zero strain stretch laminates) are styrenic block copolymer based elastic films, preferably with a thickness of 0.05 mm–0.064 mm (0.002 in–0.0025 in), such as are made by Clopay Corporation of Cincinnati, Ohio under the designation PA 18-2870; or Exxon 500 series elastic films from Exxon Chemical of Baytown, Tex. Other suitable elastomeric materials for use as the elastic panel members include "live" synthetic or natural rubber, other synthetic or natural rubber foams, elastomeric films (including heat shrinkable elastomeric films), elastomeric woven or nonwoven webs, scrims, elastomeric composites, or the like. More preferably, the elastic panel member 78 is an elastomeric scrim material. Such elastomeric scrim material is provided with a plurality of first strands that intersect a plurality of second strands, forming a net-like open structure having a plurality of apertures. Each aperture is defined by at least two adjacent first strands and at least two adjacent second strands, so that the apertures are substantially rectangular in shape. A preferred elastomeric scrim is manufactured by the Conwed Plastics Company under the designation TN2514.

In a more preferred embodiment, the elastic panel members are operatively joined in the side panel by securing them to the chassis layer 40, the belt layers 42 and 44, or both while in a substantially untensioned (zero strain) condition. At least a portion of the resultant composite stretch laminate containing the elastic panel member is then subjected to mechanical stretching sufficient to permanently elongate the nonelastic components (the chassis layer, the barrier layer, and the belt layer) of the stretch laminate. The composite stretch laminate is then allowed to return to its substantially untensioned condition. The side panel is thus formed into a "zero strain" stretch laminate. (Alternatively, the elastic panel member could be operatively joined in a tensioned condition and then subjected to mechanical stretching; although this is not as preferred as a "zero strain" stretch laminate.) As used herein, the term "zero strain" stretch laminate refers to a laminate comprised of at least two plies of material which are secured to one another along at least a portion of their coextensive surfaces while in a substantially untensioned ("zero strain") condition; one of the plies comprising a material which is stretchable and elastomeric (i.e., will return substantially to its untensioned dimensions after an applied tensile force has been released) and a second ply which is elongatable (but not necessarily elastomeric) so that upon stretching the second ply will be, at least to a degree, permanently elongated so that upon release of the applied tensile forces, it will not fully return to its original undeformed configuration. The resulting stretch laminate is thereby rendered elastically extensible, at least up to the point of initial stretching, in the direction of initial stretching. Particularly preferred methods and apparatus used for making stretch laminates utilize meshing corrugated rolls to mechanically stretch the components. Particularly preferred apparatus and methods are disclosed in U.S. Pat. No. 5,167,897 issued to Weber et al. on Dec. 1, 1992; U.S. Pat. No. 5,156,793 issued to Buell et al. on Oct. 20, 1990; and U.S. Pat. No. 5,143,679 issued to Weber et al. on Sep. 1, 1992.

The continuous belt 38 acts to dynamically create fitment forces in the pull-on diaper 20 when positioned on the wearer, to maintain the pull-on diaper on the wearer even when loaded with body exudates thus keeping the absorbent core in close proximity to the wearer, and to distribute the forces dynamically generated during wear about the waist thereby providing supplemental support for the absorbent core without binding or bunching the absorbent core in the medial panel of the pull-on diaper. The belt is designed to be elastically extensible in certain segments and at least elastically extensible, preferably elastically contractible, in other segments about the waist opening; to be elastically extensible about a portion of the leg opening; and to not be gathered or bunched in the medial panel where the absorbent core is located. The elastic extensibility of the belt also has a "force/extension wall" beyond which the belt will not elastically extend in order to allow the pull-on diaper to be more easily applied since the diaper will not stretch excessively thereby allowing the product to slide more easily over the buttocks. This "force/extension wall" is especially important for small children who self apply the product and would be unable to completely pull and position a fully stretchable product over their buttocks. The belt also manages wearing stresses better with the belt webs encircling the absorbent core. The resultant diaper is less bulky in its fit about the waist of the wearer. The lack of gathering or contraction in the belt over the absorbent core in conjunction with the continuity of the belt across the absorbent core also provides improved fit by providing a continuous normal force based on the hoop stresses generated in the belt which tends to press the absorbent core against the body during wear. Thus, the absorbent core is maintained in a closer, more comfortable, and less gapping way than those diapers which provide elastic contraction or gathering over the area of the absorbent core or those that do not provide a belt to concentrate within the span and distribute across the span the hoop stresses about the area of the absorbent core.

The seam panels 66 and 66' are those portions designed to be seamed or joined together by the manufacturer to form the defined waist opening 36 and leg openings 34. As shown in FIG. 2, the seam panels 66 and 66' extend laterally outwardly from the respective side panels 46 and 48 to the side edge 72 or 72' and generally longitudinally extend from the end edge 70 or 70' to the leg edge 71 or 71', respectively. The seam panels are preferably an extension of the chassis layer and other elements such as the belt layers and the topsheet, or any other combination of these elements. In a preferred embodiment, each seam panel is formed by portions of the chassis layer, the belt layers, the elastic panel members, and the barrier layers of the topsheet. (In the seam panel, the stretch laminate is preferably not activated by mechanical stretching, although it may be, if desired, to provide additional extensibility in this region.)

In a more preferred embodiment, the seam 32 has a predetermined seam pattern so that the seam can be torn open easily by using the tear open tab 31. Preferably, the seam 32 comprises an intermittent pattern of an individual bond or bonds grouped in clusters 4a, 4b, 4c and 4d as shown, for example, in FIG. 6. In this embodiment, the seam 32 comprises four clusters 4a–4d. Other suitable seams may have any number of clusters such as two, three, five, or more. Any shape of bond and/or cluster can be used as long as the seam can be torn open easily by using the tear open tab 31. Preferred shapes of bonds and/or clusters include a circle, an oval, a triangle and a rectangle.

The spacing between adjacent clusters 4a–4d creates gaps or unbonded portions 5a–5c in the seam 32. When the diaper 20 is worn, the seams 32 tend to buckle with the movement of the wearer. The buckling of the seams 32 at the spacings between adjacent clusters creates channels allowing air to move in and out of the diaper during use to ventilate the diaper. Thus, the unbonded portion of the seam 32, (i.e., the summation of all the individual spacing distances), determines the breathability of the seams, and thus, the breathability of the diaper 20. As the unbonded portion of the seam 32 increases so does the breathability of the diaper. However, as the unbonded portion of the seam 32 increases, the strength of the seam 32 decreases. Preferably, the unbonded portion of the seam 32 ranges from about 20% to about 65% of the total seam length, as measured from the leg opening 34 to the waist opening 36 along seam 32. Examples of suitable seams have an unbonded portion comprising about 30%, 35% or 40% of the total seam length. Unbonded portions below about 20% are generally not desirable as they do not allow a sufficient amount of air in to ventilate the diaper. Unbonded portions above about 65% are generally not desirable either as they allow sufficient amounts of air in to ventilate the diaper, but are not sufficiently strong to withstand the high forces and stresses placed on the diaper during wear.

Preferred seam patterns may include different seam strength patterns which provide varying bonding strengths between the seam panels 66 so that the seam can be torn open easily by using the tear open tab 31. In preferred embodiments, such control of the bonding strengths may be produced by changing certain amounts of polymeric material contained in the seam panels 66. To increase the bonding strength, for example, the amount of polymeric material contained in the elements forming the seam panels 66 may be increased by using higher basis weight nonwoven materials, thicker plastic films, or by introducing additional layers of materials to the seam panels 66. For example, additional plastic films or nonwoven webs may be joined in the seam panels 66. Alternatively, the layers forming the diaper may be extended beyond the intended area of seaming and folded back into the seam panel to introduce additional strata in the seam panels. Examples of these types of seams are discussed in the above-referenced U.S. Pat. No. 5,236,430.

In preferred embodiments, the tear open tab 31 can be positioned at any place along the edge of the seam panel 66. In the embodiment shown in FIG. 6, the tear open tab 31 is positioned at an outwardly extended portion of the spacing 5a which is about equally close to both the clusters 4a and 4b.

Figure 6:
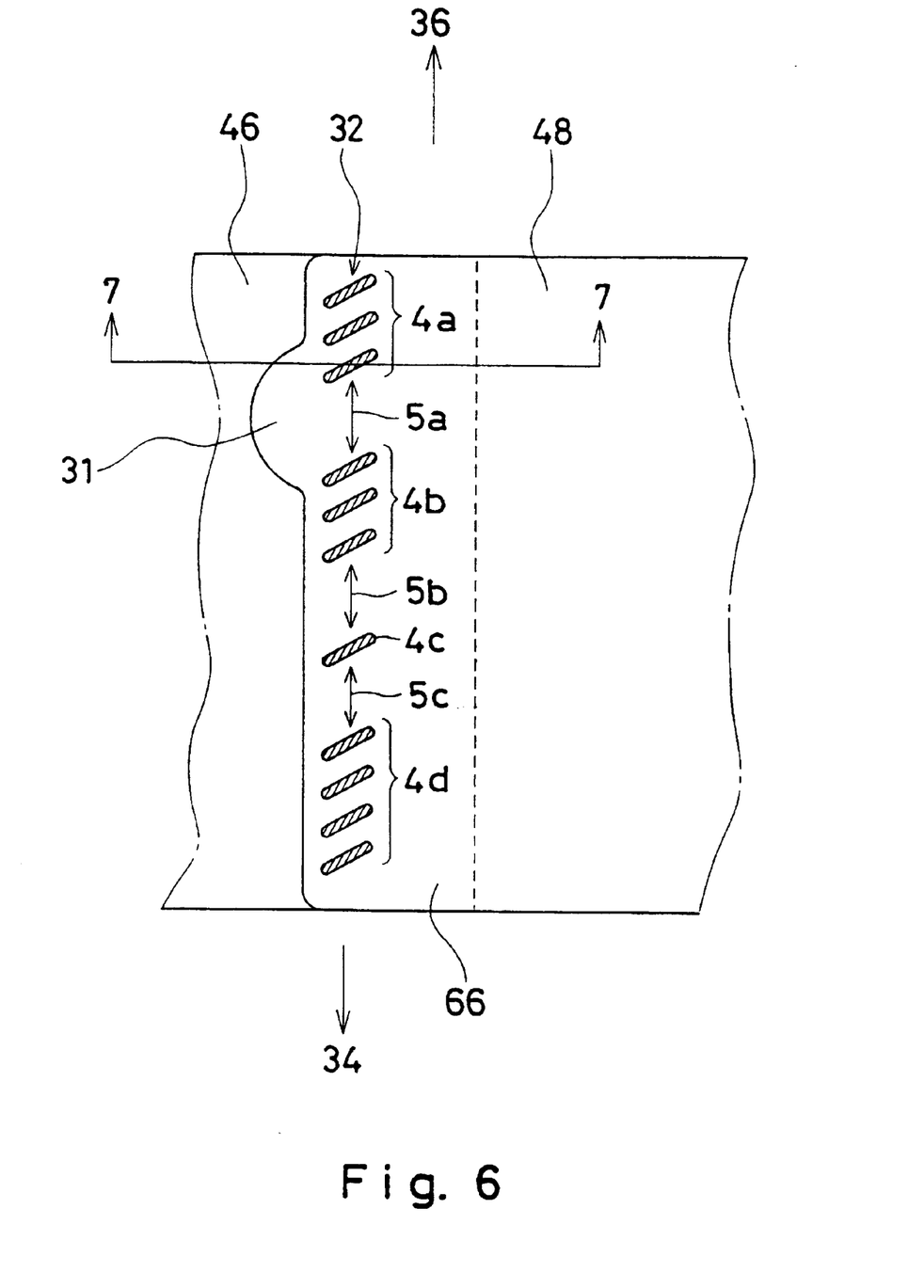
FIG. 6 is a plan view of the tear open tab and seam panel of a preferred embodiment of the present invention.

Preferably, the position of the tear open tab 31 is biased between the leg opening 34 and the waist opening 36. In a preferred embodiment, the position of the tear open tab is closer to the leg opening 34 than the waist opening 36. In a more preferred embodiment, the position of the tear open tab 31 is closer to the waist opening 36 than the leg opening 34 as shown in FIG. 6. The biased position of the tear open tab 31 indicates the user from which portion he/she should start tearing open the diaper by the fingers.

Figure 7A:
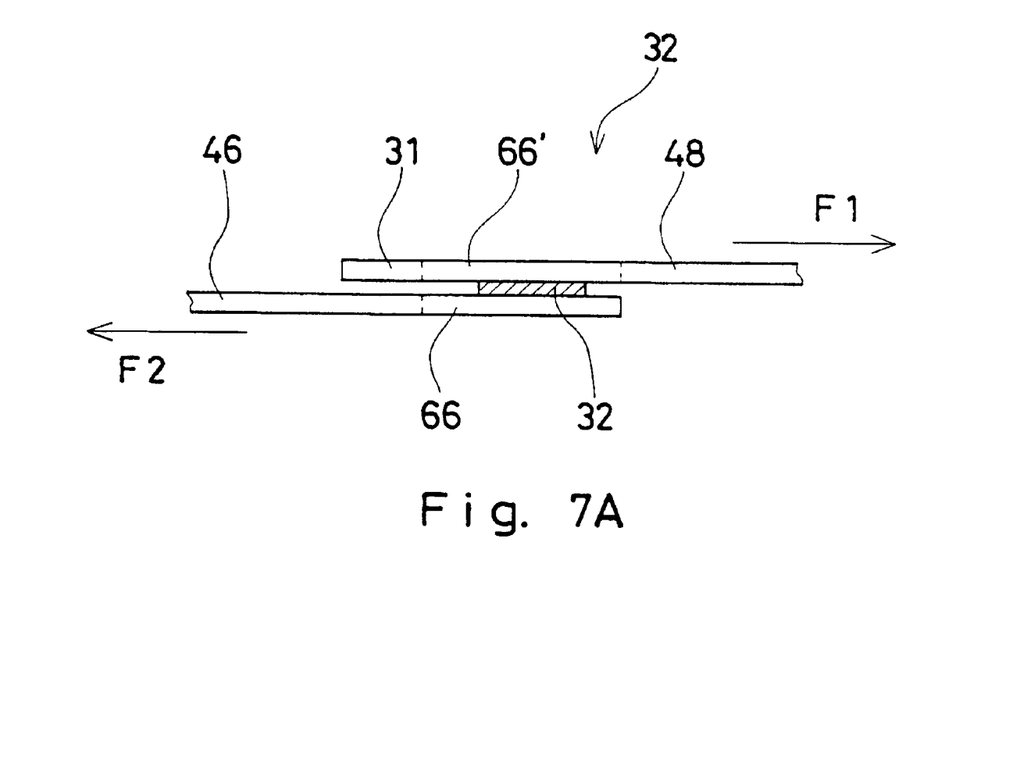
FIG. 7A is a fragmentary cross-sectional view of the seam panels taken along line 7—7 of FIG. 6, showing forces generated during wear.
Figure 7B:
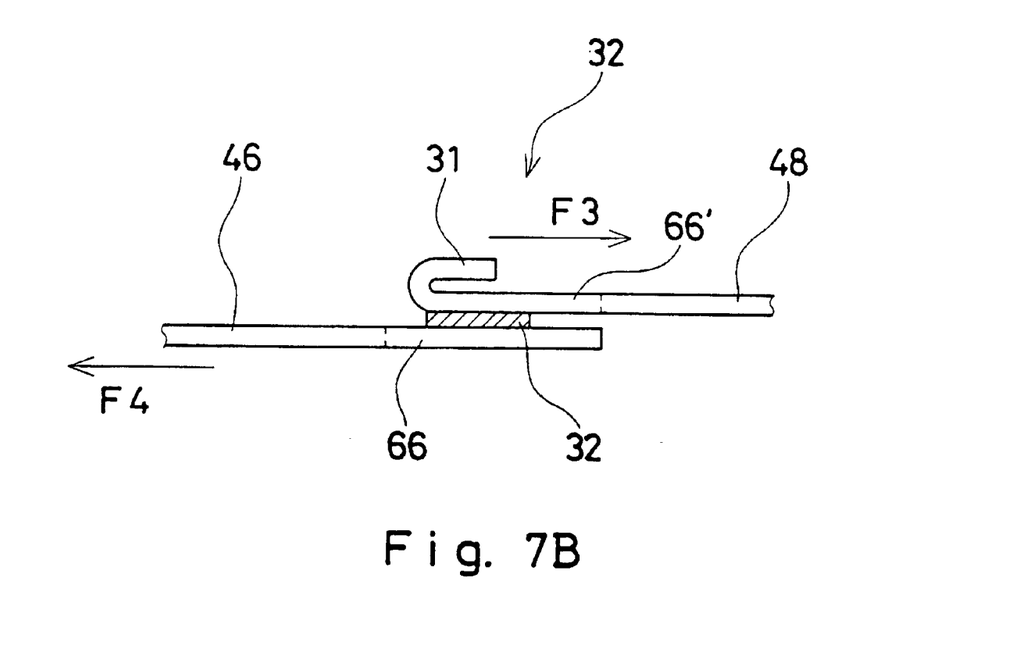
FIG. 7B is a fragmentary cross-sectional view of the seam panels shown in FIG. 7A when a pull-on diaper is torn open.

FIG. 7A shows the overlapped seam structure 32 formed by joining the seam panels 66. In this figure, one of the seam elements 32 is exaggeratedly depicted in terms of its thickness and width for the sake of explanation. The arrows F1 and F2 show the forces which are generated when the diaper 20 is worn, thus applied to the seam element 32 in the seam panels 66 and 66' through the front and back side panels 46 and 48. The overlapped seam structure provides a necessary seam strength which is required to maintain the pull-on diaper on the waist area of the wearer. FIG. 7B shows the forces F3 and F4 applied to the tear open tab 31 and the front side panel 46, respectively, when the pull-on diaper is torn open during the removal of the diaper from the wearer. As the opposite forces F3 and F4 effectively work to separate the seam panel 66 of the front side panel 46 from the seam panel 66' of the back side panel 48. The biased position of the tear open tab 31 causes a concentration of the tear open force F3 at the specific seam element 32 that is positioned closest to the leg opening 34 or the waist opening 36. Thus, the pull-on diaper 20 can be torn open from the leg opening 34 or the waist opening 36 by the application of a small amount force from the user.

Figure 8:
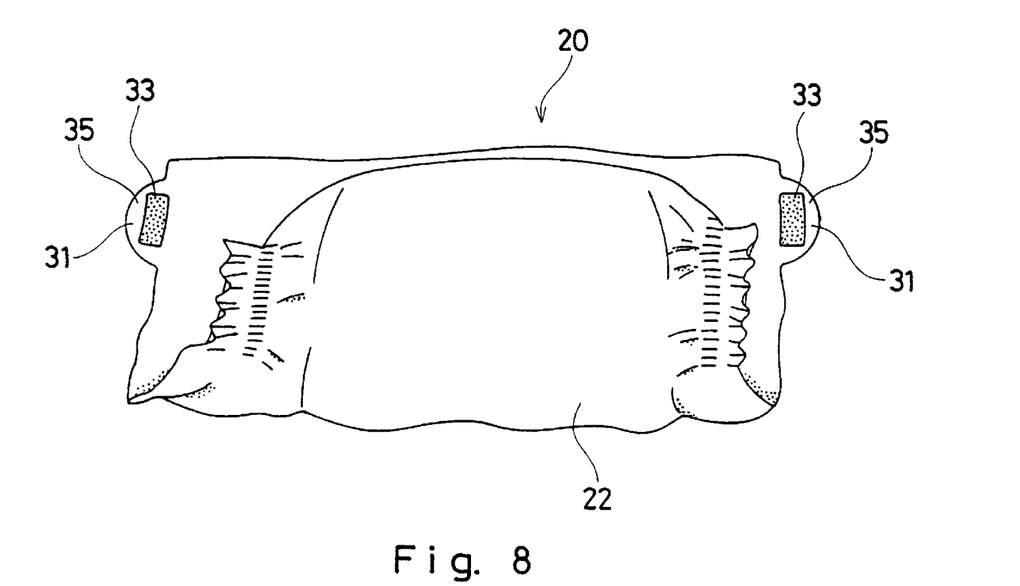
FIG. 8 is a perspective view of a preferred embodiment of a pull-on diaper when it is folded after soil.

As shown in FIG. 8, the pull-on diaper 20 has the disposal means 33 joined to the tear open tab 31 for allowing the pull-on diaper to be secured in a configuration that provides convenient disposal. In preferred embodiments, the tear open tab 31 has an inner surface 35 and an outer surface 37 (shown in FIG. 9). The disposal means 33 is joined to the inner surface 35 of the tear open tab 31 so that the disposal means 33 is positioned between the tear open tab 31 and the front side panels 46, and hidden therebetween as shown in FIG. 1.

The disposal means 33 may be any material which can allow the pull-on diaper 20 to be secured in a configuration that provides for convenient disposal. In preferred embodiments, the disposal means is a material which can engage with or stick to at least a part of the backsheet 22 or one of the front and back side panels 46 and 48 for disposal. In a preferred embodiment, the disposal means 33 comprises a mechanical fastening element which constitutes a mechanical fastener system with the backsheet 22 for disposal. In an alternative preferred embodiment, the disposal means 33 comprises a mechanical fastening element which constitutes a mechanical faster system with one of the front and back side panels 46b and 48 for disposal. The mechanical fastening element may comprise any of known means for achieving a closure such as buttons, snaps, hook fastening materials, or loop fastening materials.

The mechanical fastener system may comprise any mechanical fasteners known in the art. Exemplary fastening systems comprising mechanical fastening components are described in U.S. Pat. No. 5,058,247 entitled "Mechanical Fastening Prong" issued to Thomas Oct. 22, 1991; U.S. Pat. No. 4,869,724 entitled "Mechanical Fastening Systems With Adhesive Tape Disposal Means For Disposal of Absorbent Articles" issued to Scripps on Sep. 26, 1989; and U.S. Pat. No. 4,846,815 entitled "Disposable Diaper Having an Improved Fastening Device" issued to Scripps on Jul. 11, 1989.

In one preferred embodiment, the mechanical faster system comprises hook and loop type fasteners. As used herein, the term "hook and loop type fasteners" refers to fastening means comprising a "hook" fastening material and a complementary loop fastening material. The term "hook" is used to designate a material having engaging elements. Thus, the hook fastening material may also be referred to as a male fastener. It should also be understood that the use of the term "hook" should be non-limiting in the sense that the engaging elements may comprise any shapes as are known in the art so long as they are adapted to engage a complementary landing component. Thus, the hook fastening material may be manufactured from a wide range of materials. Further, the engaging elements may have any shape such as hooks, "T's", "mushrooms" or any other shape as are well known in the art. Suitable materials include nylon, polyester, polypropylene, or any combination of these materials. An example of preferred hook fastening material is available from Sumitomo 3M, under the trade designation XPH-5089. Yet another preferred hook fastening material is described in U.S. Pat. No. 5,058,247 entitled "Mechanical Fastening Prong" issued to Thomas Oct. 22, 1991.

In another preferred embodiment, the disposal means comprises a hook fastening material whereas the backsheet 22 or one of the front and back panels 46 and 48 comprises a loop fastening material at least at an expected landing portion. More preferably, the hook fastening material comprises a base and a plurality of engaging elements extending from the base. The hook fastening material is intended to engage with fibrous elements of a loop fastening material which is formed in or on the backsheet 22 or one of the front and back panels 46 and 48. The base may be joined to the tear open tab 31 by any suitable means. In preferred embodiments, they are directly joined with the inner surface of the tear open tab 31.

In other preferred embodiments, the backsheet 22 or the front and back panels 46 and 48 comprises a landing component (not shown) at least at the expected landing portion of the disposal means 33 for disposal. The landing component can engage with or stick to the disposal means 33. The landing component may be manufactured from a wide range of materials and configurations capable of securely engaging the engaging component. For example, the landing component may comprise identical complementary elements or distinct complementary elements. As used herein, the term "identical complementary elements" is used to define mechanical fastening systems wherein the engaging elements of the engaging component and the landing component comprise the same configuration or structure. The term "distinct complementary elements" is used herein to designate a system wherein the engaging component is different from the landing component but is engageable therewith.

In one preferred embodiment, the landing component comprises a plurality of fiber elements, such as a loop fastening material, that engage with the engaging elements of the disposal means 33. The loop fastening material may be manufactured from a wide range of materials to provide fiber elements, preferably loops. Suitable materials include woven materials, nonwovens, nylons, polyesters, polypropylenes, or any other known loop fastening materials or combination of these materials. A preferred loop fastening material comprises a number of shaped engaging elements projecting from a woven backing. An inexpensive loop fastening material and a method of making the same is described in U.S. Pat. No. 5,032,122, entitled "Loop Fastening Material For Fastening Device and Method of Making Same" issued to Noel et al., Jul. 16, 1991. Another suitable landing component material is described in U.S. Pat. No. 5,326,612 entitled "Nonwoven Female Component for Refastenable Fastening Device and Method of Making the Same" issued to David J. K. Goulait on Jul. 5, 1994.

In another preferred embodiment, the landing component has a base and a plurality of engaging elements extending from the base. The base is joined to the backsheet 22 or the front and back panels 46 and 48 at the expected landing portion. The landing component may be joined with the backsheet 22 or the front and back panels 46 and 48 by any means known in the art, including but not limited to adhesives, cohesives, heat, pressure, ultrasound, or any combination thereof. Alternatively, the landing component may be formed in a part of the backsheet 22 and the front and back panels 46 and 48.

In preferred embodiments, the backsheet 22 comprises a plastic film and a nonwoven web joined to the outer-facing surface of the plastic film so that the nonwoven web covers at least a portion, preferably more than 70%, more preferably substantially all of the outer-facing surface of the plastic film. The nonwoven web has at least a portion which forms the landing component. Preferably the plastic film is moisture permeable. The nonwoven web may be joined to the plastic film by any suitable attachment means known in the art. For example, the nonwoven web may be secured to the plastic film by a uniform continuous layer of adhesive, a patterned layer of adhesive, or an array of separate lines, spirals, or spots of adhesive. Suitable nonwoven web include a spunbond non woven web of polypropylene obtainable from Fiberweb Co., Ltd., South Carolina, USA as 13561 DAPP. Another suitable spunbond non woven web of polypropylene is obtainable from Veratec Co., Ltd., Massachusetts, USA as L4819.

In an alternative embodiment, the disposal means comprises an adhesive attachment means which can stick to or adhere to the backsheet 22 or the front and back panels 46 and 48 for disposal. In a more preferred embodiment, the adhesive attachment means comprises an adhesive positioned on the inner surface of the tear open tab 31, and a release liner positioned on the adhesive so that the adhesive will not be exposed until after the disposable pull-on diaper has been soiled. The adhesive attachment means may comprise any adhesive or glue used in the art. Preferably, pressure-sensitive adhesives are used. The release liner serves to keep the adhesive attachment means from drying out and sticking to extraneous surfaces prior to use. Any release liner commonly used for such purposes can be used.

Figure 9:
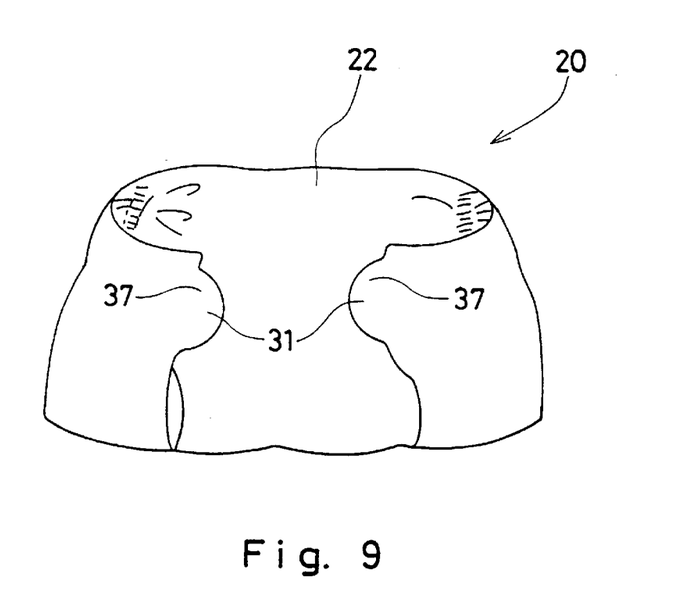
FIG. 9 is a perspective view of a preferred embodiment when the pull-on diaper shown in FIG. 8 is secured in a configuration for disposal.
Figure 10:
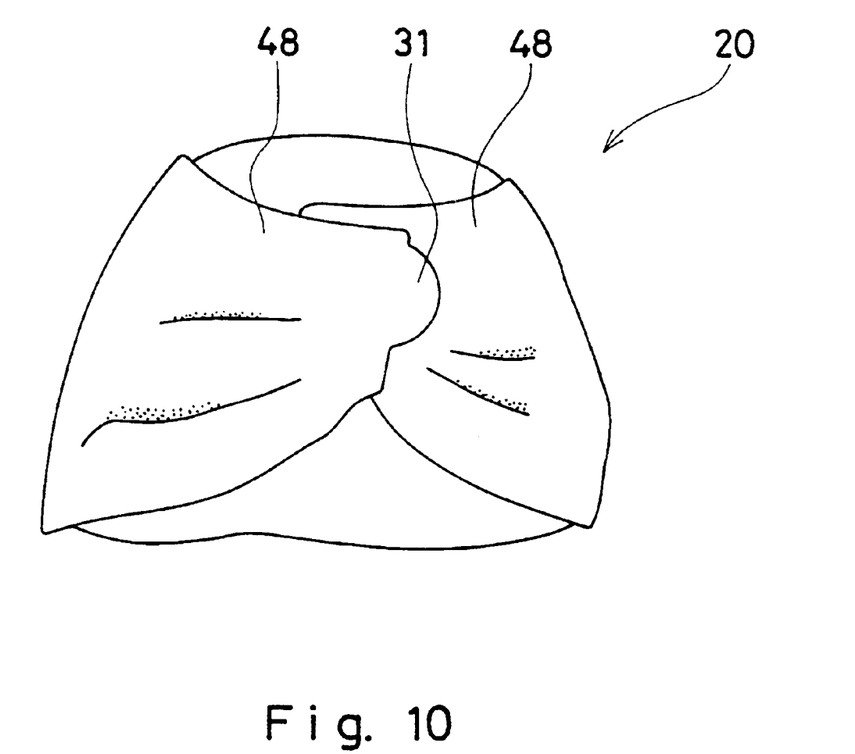
FIG. 10 is a perspective view of another preferred embodiment when the pull-on diaper shown in FIG. 8 is secured in another configuration for disposal.

After the pull-on diaper 20 is used or soiled, the soiled diaper 20 is torn open along the seams 32 by gripping the tear open tab 31 and the front side panel 46 to remove the soiled diaper 20 from the wearer. The removed diaper 20 is then folded on rolled up into a configuration for disposal to contain the contents within the soiled diaper as shown, for example, in FIG. 8. To secure the folded or rolled up diaper 20 with the disposal means 33, any configuration can be chosen. For example, the tear open tabs 31 are bonded to the backsheet 22 through the disposal means 33 (not shown) to secure the disposal configuration as shown in FIG. 9. Alternatively, one of the tear open tabs 31 of one side is bonded to the back side panel 48 of the other side through the disposal means 33 to secure the disposal configuration shown in FIG. 10. In these examples (shown in FIGS. 9 and 10), the disposal means 33 may be either a mechanical fastening element or an adhesive which is provided on the tear open tab 2 and is designed to engage with or stick to the backsheet 22 or the back side panel 48. Thus, these folded disposal configurations effectively prevent the leakage of contained urine or body exudes from the sides of the folded diaper 20.

The absorbent core 84 is preferably positioned adjacent the inner surface 76 of the chassis layer 40 and is preferably joined thereto by attachment means (not shown) such as those well known in the art. For example, the chassis layer may be secured to the absorbent core by a uniform continuous layer of adhesive, a patterned layer of adhesive, or an array of separate lines, spirals, or spots of adhesive. The attachment means preferably comprises an open pattern network of filaments of adhesive as is disclosed in U.S. Pat. No. 4,573,986 entitled "Disposable Waste-Containment Garment", which issued to Minetola and Tucker on Mar. 4, 1986. An exemplary attachment means of an open pattern network of filaments comprises several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Alternatively, the attachment means may comprise heat bonds, pressure bonds, ultrasonic bonds, dynamic mechanical bonds, or any other suitable attachment means or combinations of these attachment means as are known in the art.

The absorbent core 84 may be any absorbent means which is generally compressible, conformable, non-irritating to the wearer's skin, and capable of absorbing and retaining liquids such as urine and other certain body exudates. The absorbent core may be manufactured in a variety of sizes and shapes (e.g., rectangular, hour-glass, "T"-shaped, asymmetric, etc.) and from a wide variety of liquid absorbent materials commonly used in disposable diapers and other absorbent articles such as comminuted wood pulp which is generally referred to as airfelt. Examples of other suitable absorbent materials include creped cellulose wadding, meltblown polymers including coform, crosslinked cellulosic fibers, tissue including tissue wraps, absorbent foams, absorbent sponges, superabsorbent polymers, absorbent gelling materials, or any equivalent materials or combinations of materials. The configuration and construction of the absorbent core may also be varied (e.g., the absorbent core may have varying caliper zones, hydrophilic gradients, superabsorbent gradients, or lower average density and lower average basis weight acquisition zones; or may comprise one or more layers or structures). The total absorbent capacity of the absorbent core should, however, be compatible with the design loading and the intended use of the pull-on diaper. Further, the size and absorbent capacity of the absorbent core may be varied to accommodate wearers ranging from infants through adults.

A preferred embodiment of the absorbent core has an asymmetric, modified hourglass shape and has a body surface toward the body of the wearer (inner surface) and a diaper surface opposite the body surface. An exemplary absorbent structure for use as the absorbent core of the present invention that has been widely accepted is described in U.S. Pat. No. 5,360,420 entitled "Absorbent Structures Containing Stiffened Fibers and Superabsorbent Material" issued to Cook, Lash, Moore, & Young on Nov. 1, 1994. Preferably, the absorbent core will comprise an acquisition/distribution layer of chemically stiffened cellulosic fibers and a storage layer positioned beneath the acquisition/distribution layer comprising a mixture of wood pulp fibers and superabsorbent material such as are disclosed in U.S. Pat. No. 4,610,478 entitled "High-Density Absorbent Structures" issued to Weisman and Goldman on Sep. 9, 1986.

The topsheet 80 is positioned adjacent the body surface of the absorbent core 84 and is preferably joined to the absorbent core 84 and the chassis layer 40 by attachment means (not shown) such as those well known in the art. In a preferred embodiment, the topsheet and the chassis layer are indirectly joined together by directly joining them to the absorbent core or the elastic panel members or other elements of the pull-on diaper.

The topsheet 80 preferably comprises a three member structure such as disclosed in U.S. Pat. No. 4,795,454, entitled "Absorbent Article Having Leakage-Resistant Dual Cuffs" issued to Dragoo on Jan. 3, 1989. As shown in FIG. 5, the topsheet 80 comprises a primary layer 86 and barrier layers 88 joined to and extending laterally outwardly from the primary layer 86. The primary layer 86 is a liquid pervious material allowing liquids to rapidly penetrate through its thickness and be absorbed by the absorbent core. The two barrier layers 88 are preferably hydrophobic to prevent leakage out the sides of the diaper and are more preferably drawable to strengthen the stretch laminates.

While particular embodiments of the present invention have been illustrated and described, it would be obvious to those skilled in the art that various other changes and modifications can be made without departing from the spirit and scope of the invention. It is understood that the examples and embodiments described herein are for illustrative purpose only and that various modifications or changes will be suggested to one skilled in the art without depending from the scope of the present invention.

What is claimed is:

1. A disposable pull-on garment comprising:
   a chassis having a front region, a back region and a crotch region between the front region and the back region, the chassis comprising a liquid pervious topsheet, a liquid impervious backsheet associated with the topsheet, and an absorbent core disposed between the topsheet and the backsheet;
   front side panels extending laterally outwardly from each side of the chassis in the front region;
   back side panels extending laterally outwardly from each side of the chassis in the back region;
   seam panels each extending laterally outwardly from each of the front and back side panels;
   seams each joining the corresponding seam panels in an overlap manner to make an overlapped seam structure, thereby forming two leg openings and a waist opening;
   a tear open tab having an outer surface and an inner surface and extending laterally outwardly from at least one of the seam panels; and
   a disposal means joined to the inner surface of the tear open tab.

2. The disposable pull-on garment according to claim 1, wherein the seams comprise an intermittent seam intermittently joining the seam panels.

3. The disposable pull-on garment according to claim 1, wherein the disposal means comprises a mechanical fastening element which constitutes a mechanical fastener system with the backsheet for disposal.

4. The disposable pull-on garment according to claim 1, wherein the disposal means comprises a mechanical fastening element which constitutes a mechanical faster system with one of the front and back side panels for disposal.

5. The disposable pull-on garment according to claim 1, wherein the disposal means comprises an adhesive attachment means which can adhere to the backsheet for disposal.

6. The disposable pull-on garment according to claim 1 wherein the position of the tear open tab is biased between the leg opening and the waist opening.

7. The disposable pull-on garment according to claim 6 wherein the position of the tear open tab is closer to the waist opening than to the leg opening, or closer to the leg opening than to the waist opening.

8. The disposable pull-on garment according to claim 1 wherein the front and back side panels are elastically extensible in at least the lateral direction.

9. The disposable pull-on garment according to claim 1 wherein at least one of the front and back side panels comprises a continuous sheet material which continuously extends from the chassis.

10. The disposable pull-on garment according to claim 1 wherein the seam has a predetermined seam pattern so that the seam can be tore open easily by using the tear open tab.

* * * * *

UNITED STATES PATENT AND TRADEMARK OFFICE
CERTIFICATE OF CORRECTION

PATENT NO. : 6,302,871 B1
DATED : October 16, 2001
INVENTOR(S) : Chikaya Nakao et al.

It is certified that error appears in the above-identified patent and that said Letters Patent is hereby corrected as shown below:

<u>Column 7,</u>
Line 49, "searns" should read -- seams --.

Signed and Sealed this

Sixteenth Day of July, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.    : 6,302,871 B1
DATED         : October 16, 2001
INVENTOR(S)   : Chikaya Nakao et al.

It is certified that error appears in the above-identified patent and that said Letters Patent is hereby corrected as shown below:

<u>Title page,</u>
Item [57], ABSTRACT,
Line 16, "disposable" should read -- disposal --.

<u>Column 14,</u>
Line 61, "asymnetric" should read -- asymmetric --.

Signed and Sealed this

Second Day of September, 2003

JAMES E. ROGAN
*Director of the United States Patent and Trademark Office*